United States Patent [19]

Herrli

[11] Patent Number: 4,889,527
[45] Date of Patent: Dec. 26, 1989

[54] TWO-PIECE COUPLING DEVICE FOR FLUID EXCHANGE

[75] Inventor: Peter Herrli, Biel, Switzerland

[73] Assignee: Contempo Products, P. Herrli, Biel, Switzerland

[21] Appl. No.: 101,726

[22] Filed: Sep. 28, 1987

[30] Foreign Application Priority Data

Sep. 29, 1986 [CH] Switzerland .......................... 3890/86

[51] Int. Cl.[4] ............................................. A61M 1/06
[52] U.S. Cl. ...................................... 604/29; 604/905; 604/250; 604/283
[58] Field of Search .................. 604/29, 905, 250, 283; 285/314, 315, 320

[56] References Cited

U.S. PATENT DOCUMENTS

| 2,789,838 | 4/1957 | Palm | 285/315 |
| 4,256,106 | 3/1981 | Shoor | 604/905 |
| 4,334,551 | 6/1982 | Pfister | 137/614.03 |
| 4,557,261 | 12/1985 | Rugheimer | 604/283 |
| 4,738,668 | 4/1988 | Bellotti et al. | 604/905 |
| 4,745,950 | 5/1988 | Mathieu | 604/905 |

FOREIGN PATENT DOCUMENTS 2118440 11/1983 United Kingdom .

OTHER PUBLICATIONS

"CAPD—Safe Lock 5F Take-Off-System," spec sheet of Fresenius AG, Oberursel, West Germany (undated).

Primary Examiner—C. Fred Rosenbaum
Assistant Examiner—Kathleen A. Daley
Attorney, Agent, or Firm—Zarley McKee, Thomte, Voorhees & Sease

[57] ABSTRACT

A two-piece coupling device is provided for the exchange of liquid or gaseous material. The first coupler has a sleeve with a longitudinal central passage and an axially projecting extension with at least one step. A jacket at least partially surrounds the extension. The first coupler also has a detachable fastener and a resilient tubular connection which is secured at one end within the jacket. The second coupler has a detachable fastener which cooperates with the fastener of the first coupler, and a hollow projection extending toward the first coupler. The hollow projection surrounds the entire extension of the sleeve of the first coupler, as well as part of the jacket. The device also includes an automatic blocking element for preventing the flow of the media through the tubular connection when the first coupler is separated from the second coupler.

4 Claims, 5 Drawing Sheets

TWO-PIECE COUPLING DEVICE FOR FLUID EXCHANGE

This invention relates to connectors, and more particularly to a two-piece coupling device for the exchange of liquid or gaseous media, of the type having a first and a second coupling part with one flow duct each, the two coupling parts being detachable from one another, and one hose line each being connected in the region of their outer ends.

Such a two-piece coupling device is used particularly in a system for carrying out the ambulatory dialytic withdrawal of metabolic products excreted by the damaged kidneys of a patient. In such a case, waste dialysis solution is drained out of the patient's peritoneal cavity, and fresh dialysis solution is thereafter introduced into the cavity.

Ambulatory peritoneal dialysis can be carried out by a kidney patient himself twenty-four hours a day and seven days a week, without interruption, e.g., with CAPD at least four times a day. The fresh solution to be introduced into the patient's peritoneal cavity has a volume of at least two liters. The waste solution is drained into an empty bag. By means of ambulatory dialysis, metabolic substances secreted by the patient's damaged kidneys are removed from his body, and during the exchange cycles he can go on with his usual daily activity.

In the system for carrying out peritoneal dialysis, the catheter (usually a Tenckhoff catheter) and the connecting tube joined to it convey the waste dialysis solution in one direction and the fresh dialysis solution in the opposite direction. The coupling device is connected into this system. The course of operations when the dialysis solution is exchanged is always that the waste solution is drained out of the patient's peritoneal cavity first, and then the fresh solution flows in the opposite direction through the same catheter and tubing system.

It is to be presupposed that the air outside the coupling device is contaminated, whereas the liquids in the catheter and in the coupling device are assumed to be sterile.

In order to prevent the problem of the spread of contamination by bacterial germs in the apparatus used for peritoneal dialysis, a CAPD-Safe-Lock 5F has been developed by Fresenius AG of Oberurstel, West Germany. In the first coupling part of this two-piece coupling device, in which the catheter or its extension piece terminates, a flow duct is formed in which a spring-biased valve is accommodated. The second coupling part, in which both the tube for supplying fresh dialysis solution ad the tube for draining off the waste solution are accommodated, is designed to be screwed to the first coupling part and locked by means of a bayonet system.

In the first bayonet position, a quantity of fresh dialysis solution flows around the connection parts and is then drained off into the tube for waste solution. In the second bayonet position the springbiased valve is pressed down from its seat position by the projecting end portion of the supply tube, so that the waste solution can be drained out of the patient's peritoneal cavity into the tube provided for that purpose; during this time, the opening of the end portion of the supply tube remains closed by the valve. In the third bayonet position, the valve is opened by the mouth of the end portion of the supply tube, and the fresh dialysis solution can flow into the catheter.

A danger exists that air entrapped in the coupling device when it is connected may reach the patient's peritoneal cavity along with the fresh solution. Furthermore, if the flow is turbulent, fibrin is formed and carried off together with the waste solution. This fibrin can be deposited on the coil spring and the valve and stop up the flow duct. The spring and the valve are thereby hindered in their operation, and it may result that the valve does not tightly close the outlet from the end portion of the supply tube.

It is an object of this invention to provide an improved two-piece coupling device which precludes any contamination of the liquids flowing through it.

A further object of this invention is to provide a coupling device wherein any outside air entrapped in the device is prevented from entering the catheter or the patient's peritoneal cavity and is completely evacuated along with the waste dialysis solution flowing out of the coupling device.

Another object of this invention is to provide a coupling device wherein any solids which may be eliminated by the patient and transported by the waste dialysis solution are certain to pass all the way through the coupling device.

Still another object of this invention is to provide a coupling device which is simple to use in order to prevent incorrect manipulation.

To this end, in the two-piece coupling device according to the present invention, of the type intially mentioned, the first coupling part comprises a sleeve having a longitudinal central passage and an axially projecting extension including at least one step, a jacket surrounding the extension at least partially, a first detachable fastening means, and a resilient hollow body, one end of the hollow body being secured in the jacket, means are provided for automatically blocking the passage of the media through the hollow body when the first coupling part is separated from the second, and the second coupling part has a second detachable fastening means co-operating with the first coupling part, this projection surrounding the entire extension of the sleeve and part of the jacket.

The present invention further includes a system utilizing the two-piece coupling device for carrying out peritoneal dialysis on patients having damaged kidneys.

A preferred embodiment of the invention will now be described in detail with reference to the accompanying drawings, in which.

Figure 1:
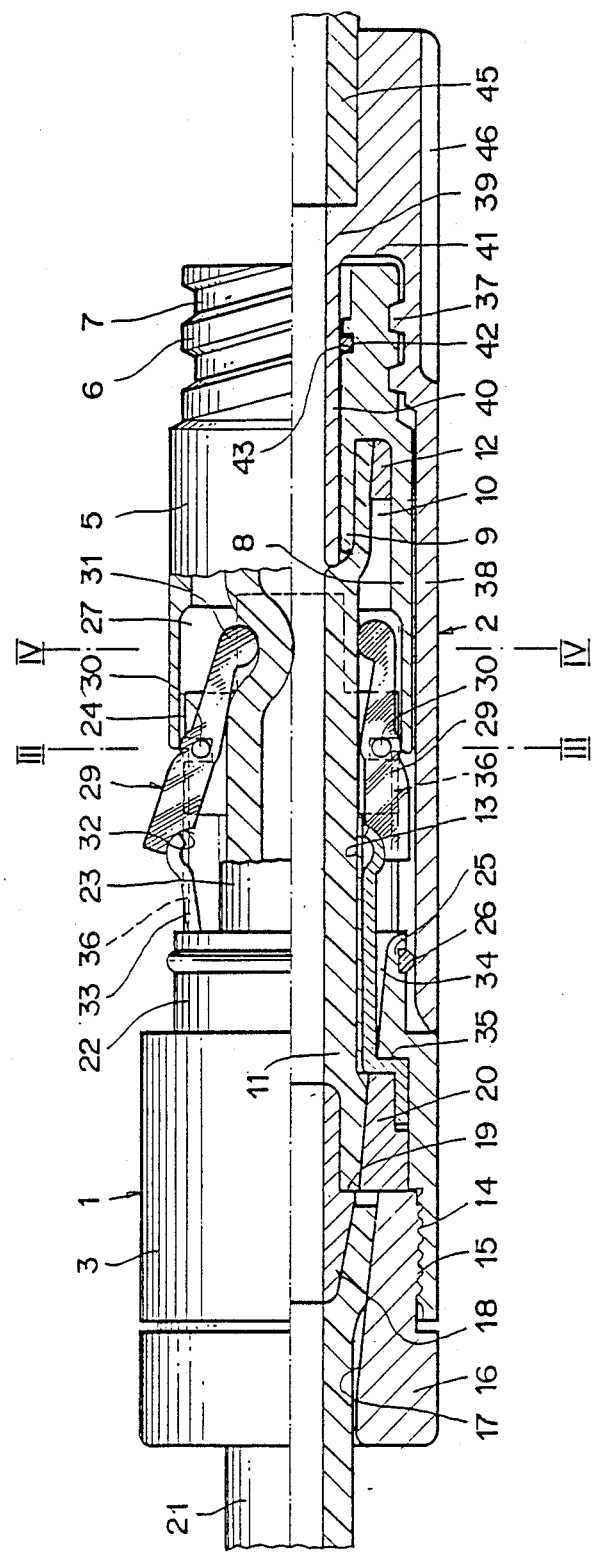
FIG. 1 is a longitudinal section through both halves of a coupling device according to the invention, the upper half of the drawing showing only one of the coupling parts and the lower half showing the two coupling parts assembled.

The illustrated embodiment of a coupling device according to this invention comprises a first coupling part 1 and a second coupling part 2 and is shown partially in section in FIG. 1. The upper half of FIG. 1 shows only coupling part 1, while the lower half shows coupling part 2 attached to coupling part 1. Coupling part 1 comprises a sleeve 3, a multi-stepped extension 4 adjacent thereto, and a jacket 5 surrounding extension 4 for the most part. The end of jacket 5 remote from extension 4 has a prolongation 7 provided with an external thread 6. Adjacent to the inside of prolongation 7 is an inside wall 9 concentric with the outer wall 8 of jacket 5, which walls bound an annular space 10. Projecting into space 10 is one end of a resilient hollow body, e.g., a tubing connection 11, secured in annular space 10 by means of a clamping ring 12. Tubing connection 11 extends through a central longitudinal passage 13 in extension 4 and sleeve 3 and ends in about the middle of sleeve 3.

The end of sleeve 3 remote from extension 4 is bored out and has an internal thread 14 into which an external thread 15 of an end member 16 of coupling part 1 is screwed. End member 16 has a central bore 17 which increases in diameter toward the inside. Concentrically disposed within sleeve 3 is a thrust ring 18 projecting partially into passage 13 and bore 17. The inner half of ring 18 is uniformly thick, while the outside diameter of the outer half increases toward the inside and forms a bearing shoulder 19 approximately in the middle. The end of tubing connection 11 projecting into sleeve 3 rests against shoulder 19.

This end portion of tubing connection 11 is encircled by a clamping ring 20 having a wedge-shaped cross-section. Ring 20 is pressed by end member 16 toward the right, as viewed in FIG. 1, the portion of tubing connection 11 between clamping ring 20 and the inner half of thrust ring 18 having the uniform thickness being held fast within sleeve 3 by a clamping effect.

The distal end of a catheter 21 (e.g., a Tenckhoff catheter) extends through central bore 17 of end member 16 and surrounds the half of thrust ring 18 which increases in diameter toward the inside. The distal end of catheter 21 is thereby held fast within sleeve 3 by a clamping effect as well.

Figure 2:
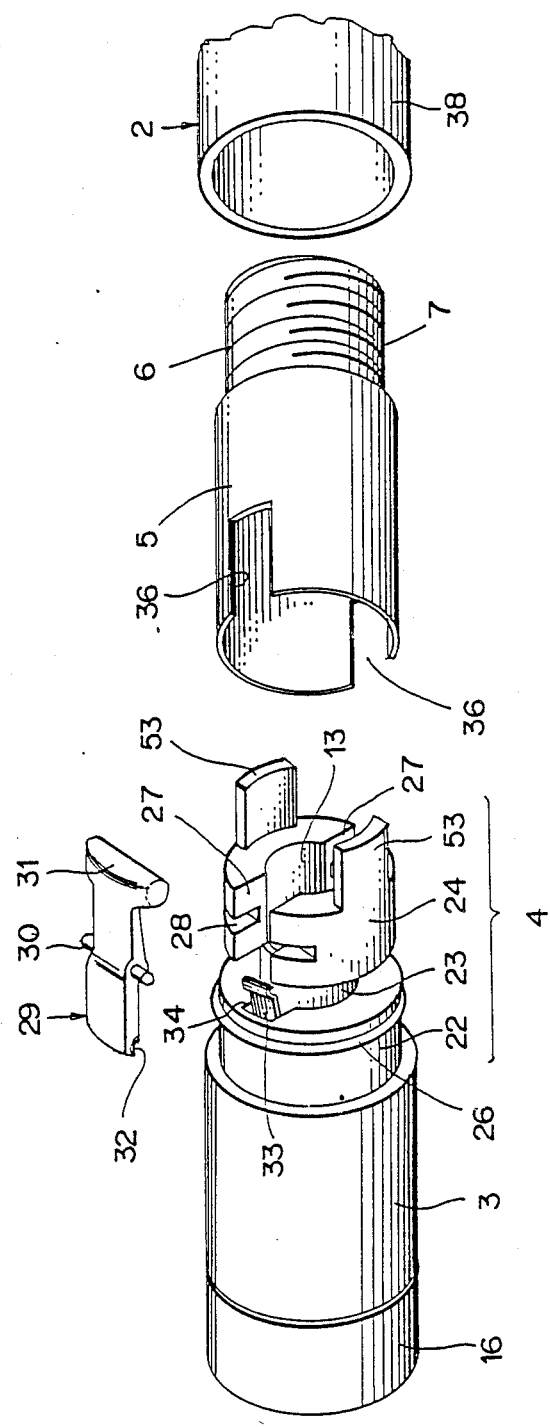
FIG. 2 is an exploded perspective view of the first and second coupling parts.

Extension 4 has three sections 22, 23, and 24 of different outside diameters (cf. FIG. 2). The outside diameter of the first section 22 is less than that of sleeve 3 but greater than the outside diameter of the third section 24, which is connected to section 22 by the second section 23. The outside diameter of the second section 23 is less than that of the third section 24.

Section 22 includes a circumferential groove 25 containing a sealing ring 26. At two opposite points on section 24 there are recesses 27 running both radially and axially. Notches 28 extend at right angles to recesses 27. Disposed in each of the recesses 27 is a rocker 29 pivotable about an axis running at right angles to the longitudinal axis of the coupling device. Each rocker 29 has two laterally projecting pivot pins 30 supported in notches 28 (FIG. 2).

The end of rocker 29 projecting over the third section 24 takes the form of a clamping jaw 31 intended to act upon tubing connection 11. The other end of rocker 29 has an arcuate hollow 32 co-operating with the free end of a spring element 33. This spring element extends substantially parallel to the longitudinal axis of coupling part 1 through a guide groove 24 running in the aforementioned longitudinal direction within the first section 22 of extension 4 and sleeve 3. The end of spring element 33 opposite its free end is bent twice and clamped fast between a bearing shoulder 35 within sleeve 3 and the small end face of clamping ring 20. Spring element 33 is biased in such a way that the end of rocker 29 having the arcuate hollow 32 is pressed radially outward by the free end of element 33.

Jacket 5 has two oppositely disposed slots 36 through each of which part of the associated rocker 29 projects when the second coupling part 2 is removed from the first coupling part 1. The outside diameter of section 24 of extension 4 is substantially the same as the inside diameter of jacket 5, so that the latter is force-fitted over section 24 and rigidly joined thereto.

The second coupling part 2 has an internal thread 37 and an adjacent tubular socket 38. When coupling parts 1 and 2 are assembled, internal thread 37 of coupling part 2 is screwed onto external thread 6 of prolongation 7 of jacket 5. The inside diameter of socket 38 is somewhat greater than the outside diameter of section 22 of extension 4 and the outside diameter of jacket 5. The length of socket 38 is such that when coupling part 2 is screwed onto external thread 6 completely, the end of socket 38 reaches almost to sleeve 3. This ensures that the end portion of socket 38 co-operates with sealing ring 26 in groove 35 of section 22. The end of coupling part 2 opposite socket 38 includes, adjacent to internal thread 37, a rib 39 protruding radially inward and supporting a cylindrical wall disposed concentrically with socket 38. The inside diameter of cylindrical wall 40 is equal to the inside diameter of tubing connection 11. Wall 40, internal thread 37, and part of socket 38 bound an annular chamber 41 into which part of jacket 5 projects, together with external thread 6 on prolongation 7.

On the inside of prolongation 7 of jacket 5 there is a circumferential groove 42 containing a sealing ring 43. Sealing ring 26 on section 22 and sealing ring 43 in prolongation 7 form an effective bacteria barrier, i.e., bacteria are prevented from reaching the flow duct from outside. The bacteria barrier is particularly fully effective when the axial distance between ring 26 and the pivoting axis of rocker 29 is less than the distance between the free end of cylindrical wall 40 and ring 43.

A bore 44 in the outer end region of coupling part 2, i.e., between rib 39 and the outer end of coupling part 2, has a larger inside diameter than wall 40. Cemented in bore 44 is a tube 45. To improve the grip, longitudinal ridges 46 are regularly distributed around the periphery of this end region of coupling part 2. Similar ridges may preferably be provided on the outside of sleeve 3 as well.

Figure 3:
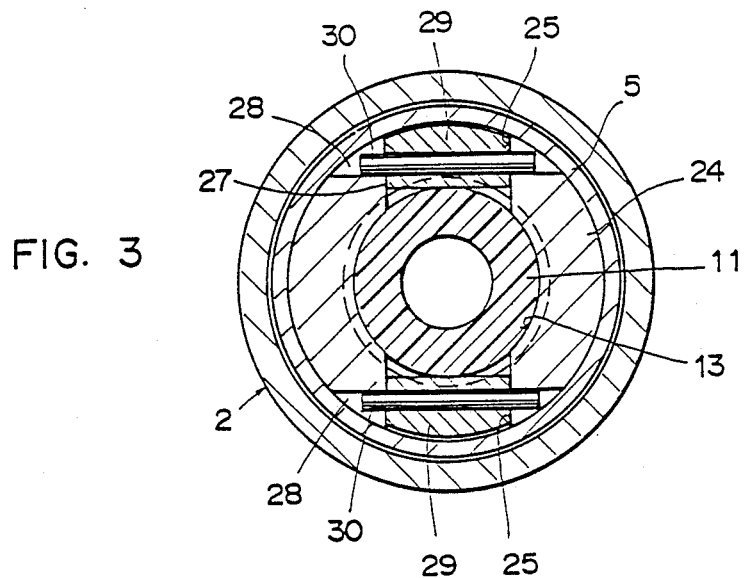
FIG. 3 is a section taken on the line III—III of FIG. 1.

FIG. 3 is a section taken on the line III—III of FIG. 1 through the complete coupling device with parts 1 and 2 assembled. In this state, tubing connection 11 is not pressed together, and the flow duct of the coupling device has the same round cross-section all along because the inside diameters of catheter 21, thrust ring 18, tubing connection 11, cylindrical wall 40, and tube 45 are all the same. The flow of liquid through the coupling device is therefore laminar, and no fibrin can form; moreover, there is no danger that any solids conveyed through catheter 21 with the dialysis solution can stop up the coupling device.

Figure 4:
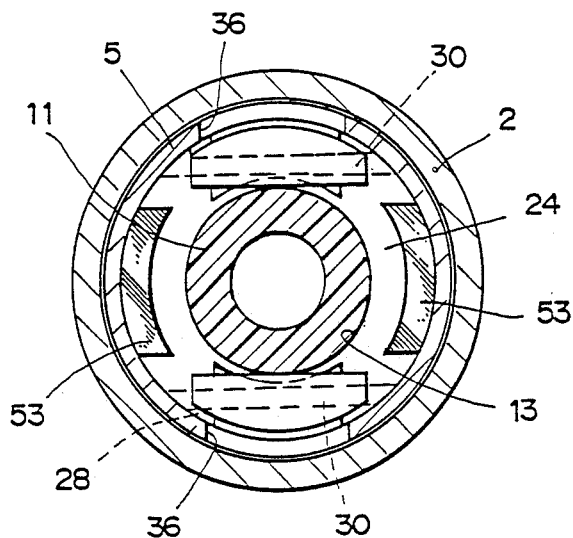
FIG. 4 is a section taken on the line IV—IV of FIG. 1 with the two coupling parts assembled.

FIG. 4 is a section taken on the line IV—IV of FIG. 1 in the region of clamping jaws of rockers 29. Because when coupling parts 1 and 2 are assembled, socket 38 presses the ends of rockers 29 opposite jaws 31 radially inward against the bias of spring elements 33, jaws 31 rest only lightly or not at all against the outside of tubing connection 11. Thus, the flow of liquid through tubing connection 11 is not hindered in any way.

Figure 5:
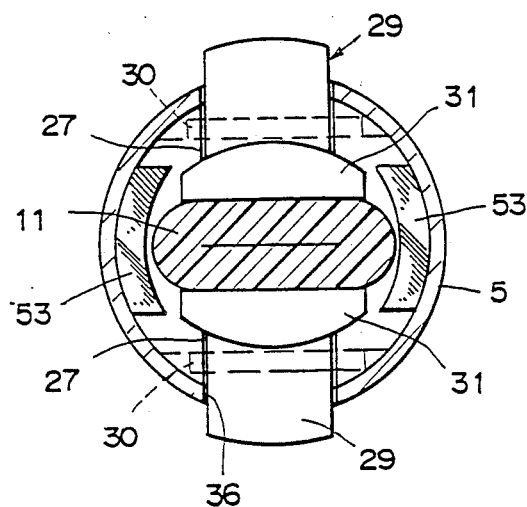
FIG. 5 is a section taken on the line IV—IV of FIG. 1 with the second coupling part removed.

If coupling part 2 is separated from coupling part 1, spring elements 33 can press the ends of rockers 29 opposite jaws 31 radially outward. As a result, the two clamping jaws 31 move radially inward until tubing connection 11 is pressed completely flat, as shown in FIG. 5, which is a section taken on the same line as FIG. 4. In order to keep tubing connection 11 from shifting laterally, diametrically opposite projections 53 are provided on the end face of section 24 of extension 4. Projections 53 are responsible for keeping the compressed tubing connection 11 between clamping jaws 31.

Figure 6:
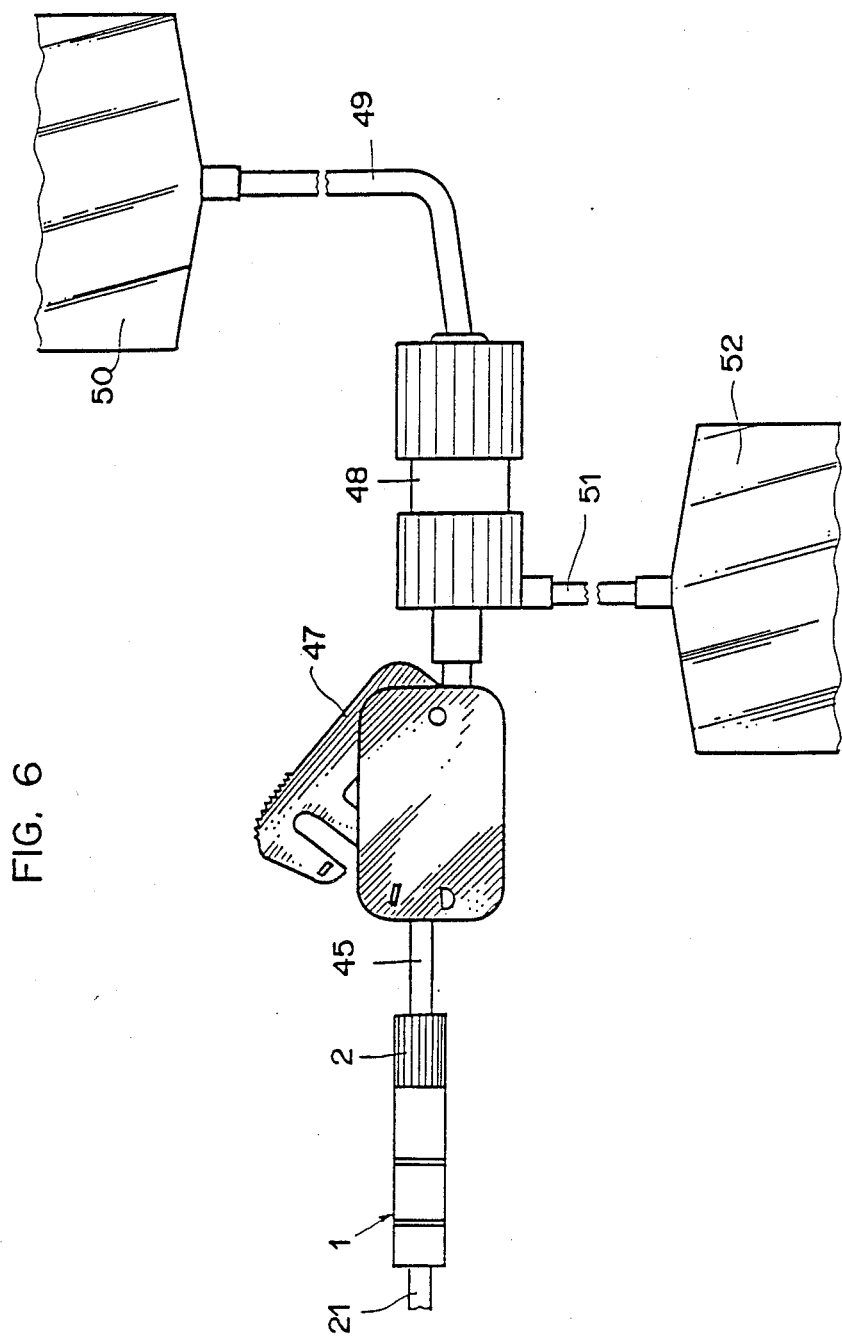
FIG. 6 is a diagrammatic elevation of a system for carrying out ambulatory peritoneal dialysis.

FIG. 6 illustrates a system for carrying out peritoneal dialysis on patients with damaged kidneys, utilizing the two-piece coupling device described above. part of catheter 21 leading to the patient's peritoneal cavity is shown connected to coupling part 1. Also shown are a connecting tube 45, a device 47 for clamping and severing tube 45, a three-way connector 48, a supply tube 49 for supplying fresh dialysis solution from a bag 50, and a drain tube 51 for draining waste dialysis solution into a bag 52. The metabolic products excreted by the patient's damaged kidneys are carried out of the peritoneal cavity by the waste dialysis solution, whereafter fresh dialysis solution is introduced into the patient's peritoneal cavity in the opposite direction.

The flow duct through the coupling device and the connecting tube has a constant inside diameter over its entire length. Assuming a constant diameter of 3 mm in the Tenckhoff catheter, the flow duct in the coupling device has the same diameter of 3 mm. The rate of discharge of the waste solution thereby remains constant everywhere, and this is an important prerequisite for ensuring that all solids conveyed through the Tenckhoff catheter are carried along in the same way through the coupling device. Furthermore, air entrapped in the flow duct during the coupling operation is thereby reliably evacuated with the waste dialysis solution drained off.

In another embodiment of the coupling device according to the present invention, tubing connection 11 may be the distal end portion of catheter 21. In this case, thrust ring 18 of the embodiment illustrated in FIG. 1 may be dispensed with. In still another embodiment, the two coupling parts may have a substantially rectangular cross-section in order to reduce the thickness of the coupling device. Instead of the external and internal threads, the two coupling parts will then have cooperating snap closures which may be lockable, if desired, in order to prevent any accidental separation of the coupling parts.

What is claimed is:

1. A two-piece coupling device for the exchange of liquid or gaseous media, of the type having a detachably connectible first coupling part and second coupling part, each including a flow duct, and two tubes respectively connected to said coupling parts, wherein the improvement comprises:
    a said first coupling part including a sleeve a longitudinal central passage and an axially projecting extension including at least one stepped portion, a jacket at least partially surrounding said extension, a first detachable fastening means, and a resilient hollow body secured at one end in said jacket,
    automatic blocking means for preventing the flow of the media through said hollow body when said first coupling part is separated from said second coupling part,
    a said second coupling part including a second detachable fastening means co-operating with said first detachable fastening means co-operating with said first detachable fastening means and a hollow projection extending toward said first coupling part, said projection entirely surrounding said extension and partially surrounding said jacket;
    said jacket including an axial prolongation, said first fastening means being an external thread on said prolongation, and said second fastening means being an internal thread with said second coupling part; and
    the end of said hollow body remote from said jacket being secured in said sleeve, and said extension comprising first, second and third sections, said first section being directly adjacent to and smaller in diameter than said sleeve and including a circumferential groove and a sealing ring disposed in said groove, said second section being directly adjacent to and smaller in diameter than said first section, said third section being smaller in diameter than said first section, directly adjacent to and larger in diameter than said second section, and including two diametrically opposed axially and radially extending recesses, part of said automatic blocking means being disposed in said recesses.

2. The coupling device of claim 1, wherein said automatic blocking means comprise two oppositely disposed rockers and at least two spring elements respectively acting upon one end of each of said rockers, the other ends of said rockers being designed as clamping jaws for compressing said hollow body.

3. The coupling device of claim 2, wherein said third section of said extension further includes four notches, two said notches being respectively disposed adjacent to and at right angles to each of said recesses, and each of said rockers comprising two pivot pins respectively disposed in said two notches.

4. The coupling device of claim 3, wherein said third section of said extension includes an end face remote from said second section, further comprising two opposed projections fixed to said end face and disposed laterally with respect to said clamping jaws for preventing lateral displacement of said hollow body upon compresseion thereof by said clamping jaws.

* * * * *